United States Patent [19]
Arnold et al.

[11] Patent Number: 4,573,478
[45] Date of Patent: Mar. 4, 1986

[54] AUTOMATIC PULSE RATE TRIGGER-SOURCE SELECT CIRCUIT

[75] Inventors: Jeffrey M. Arnold, Ridgewood; James R. Brosnahan, River Edge; Terrence H. Koong, Teaneck; Thomas A. Mans, Harrington Park; Theodore A. Milo, Teaneck, all of N.J.

[73] Assignee: Datascope Corporation, New York, N.Y.

[21] Appl. No.: 516,266

[22] Filed: Jul. 22, 1983

[51] Int. Cl.⁴ .............................................. A61B 5/00
[52] U.S. Cl. .................................... 128/670; 128/687; 128/706
[58] Field of Search .............. 128/670, 687, 689, 698, 128/706

[56] References Cited
U.S. PATENT DOCUMENTS 3,858,574  1/1975  Page ................................... 128/689
3,952,731  4/1976  Worstencroft ..................... 128/702
4,299,234  11/1981  Epstein et al. ..................... 128/698

Primary Examiner—William E. Kamm
Attorney, Agent, or Firm—Fitzpatrick, Cella, Harper & Scinto

[57] ABSTRACT

Disclosed herein is a circuit for automatically selecting between an ECG heartbeat signal source and a pressure/pulse signal source depending on which of the two sources is the most periodic between three successive heart beats. A pair of microprocessor internal timers commence a count-up cycle in response to a first detected heart beat from each of the two respective sources, after which count-down cycles are started in response to the next successive detected heart beats. The counting of the timers is then stopped in response to the third successive detected heart beats from the two sources and a comparison is provided to determine which of the two sources is most periodic, and should be used to trigger a heart rate monitor.

4 Claims, 6 Drawing Figures

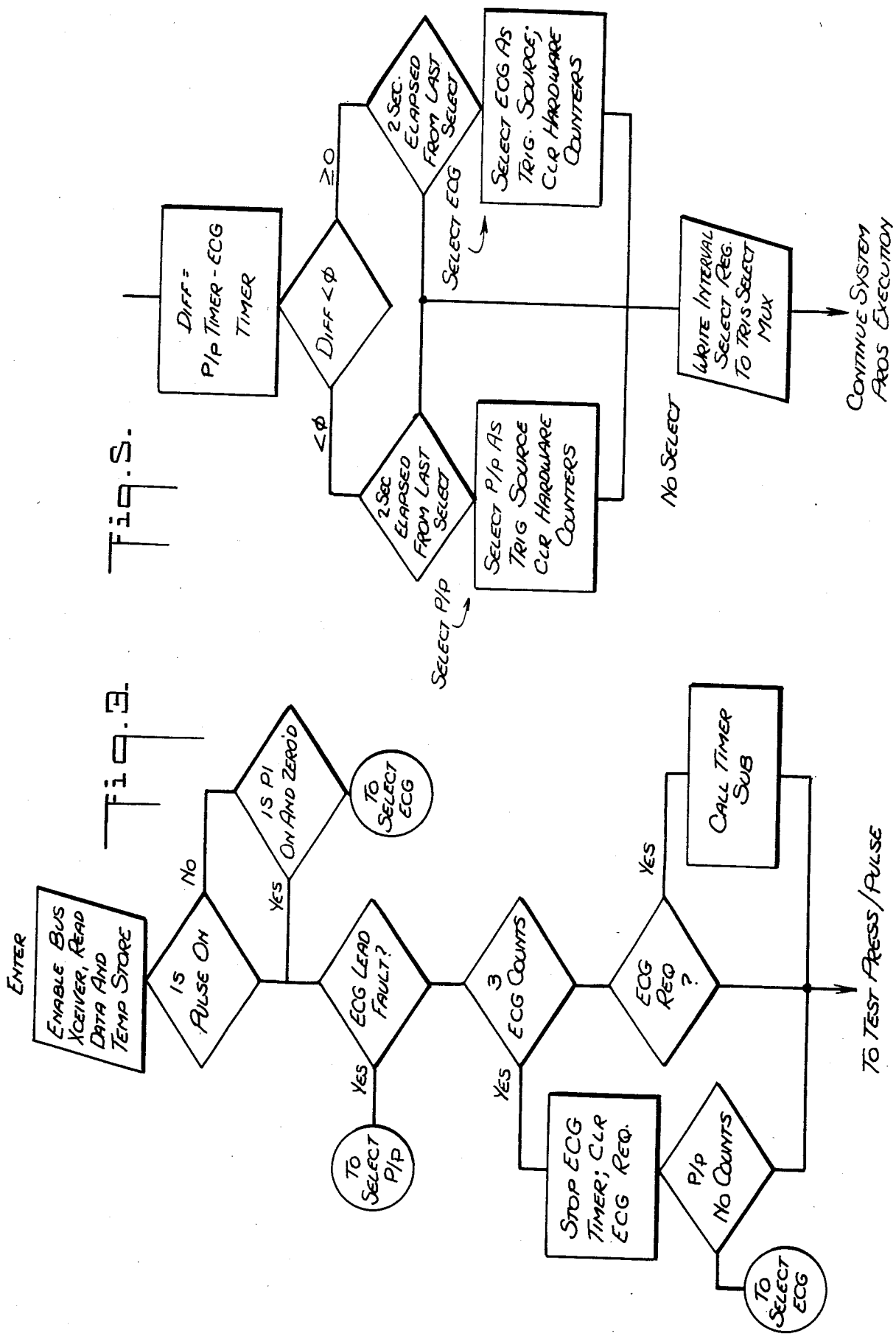

AUTOMATIC PULSE RATE TRIGGER-SOURCE SELECT CIRCUIT

BACKGROUND OF THE DISCLOSURE

One of the primary functions of a cardiac monitor is to reliably measure the heart rate of a patient. Conventionally, electrocardiographic electrodes are used to sense the patient's heart rate, and the signal derived from such electrodes is applied to the cardiac monitor. A problem arising from the use of such electrodes is that muscle twitch, or muscle artifact, may generate signals in the electrodes which will cause erroneous heart rate readings. It is possible to avoid such electrode problems by sensing the patient's pulse rate with a pressure transducer connected invasively or a pulse device attached to the finger or ear of the patient. However, random erroneous signals may also be detected by a pressure transducer or pulse sensor as a result, for example, of external pressure applied to the patient's body during the monitoring procedure.

A solution to the problems arising from these two forms of sensing a patient's pulse rate, in the past, was to provide a switching device to enable the user to select either the ECG source or the pressure source for triggering a heart rate meter.

An object of the present invention, however, is to provide an automatic selecting circuit which senses the most periodic or reliable one of the two heart rate sources and which applies that selected source as the input signal to the cardiac monitor.

SUMMARY OF THE INVENTION

In accordance with the invention, apparatus is provided for coupling an ECG waveform and a pressure response waveform to a selection circuit which senses the relative constancy or periodicity of the two sensed signals. The circuit includes a microprocessor having timers for timing the successive periods between pulses applied to the apparatus by the ECG electrodes and the pressure/pulse source, wherein the source having the higher degree of periodicity is supplied as the trigger-source utilized for indicating the patient's heart rate. In a preferred embodiment of the invention, the microprocessor is provided with timers which count the number of cycles (for example, from a 60 Hz signal), during the interval from one heart beat to the next, and which then decrement at the same rate during the succeeding interval until a third heart beat is sensed. This sequence is performed for both of the heart rate signal sources, and the counter with the lower number at the end of the three required heart beats is determined to be most accurate, and is used as the source of heart rate pulses utilized by the cardiac monitor.

In this regard, an assumption has been made that artifact signals will not be produced with the normal peridicity of a patient's heart beat, wherefore it is highly unlikely that a pulse would occur at the exact center of the interval between two actual heart beat pulses. Also the changes are even more remote that such an artifact pulse would occur in synchronism with the patient's heart beat. Accordingly, the count up and count down system for timing the periodicity provides an accurate result.

BRIEF DESCRIPTION OF THE DRAWING

A preferred embodiment of the invention will be described herein in conjunction with the accompanying drawings, wherein:

FIGS. 3–6 constitute flow charts illustrating the operation of the circuitry depicted in FIG. 1.

DETAILED DESCRIPTION OF A PREFERRED EMBODIMENT OF THE INVENTION

Figure 1:
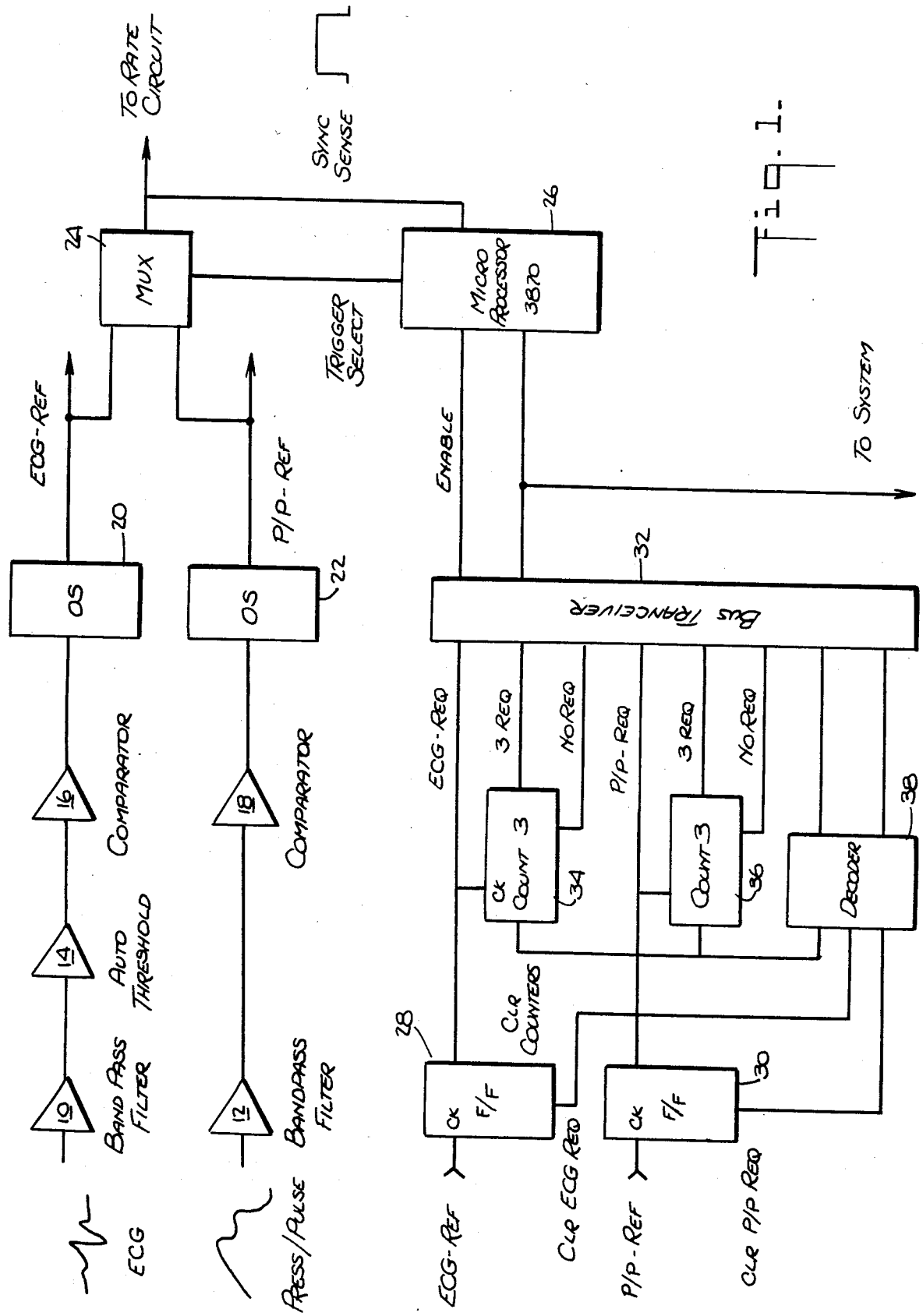
FIG. 1 shows a block diagram of one embodiment of the invention.

A cardiac monitor trigger select circuit is depicted in FIG. 1 of the drawing wherein an ECG waveform and a pressure or pulse generated waveform are connected to separate band-pass filters 10 and 12 designed to pass only the frequencies embodied in the respective source waveforms. In accordance with the symbols used herein PI designates an invasive pressure transducer input; PULSE designates a source using an external pulse sensor; and, P/P indicates either of the above two sources.

In the input circuitry of the trigger select circuit for the ECG source, an auto threshold circuit 14 is provided for limiting the passage of input signals having an amplitude below a predetermined threshold. In this regard the threshold circuit 14 is set to ensure passage of the r-portion of the ECG waveform. Both of the input lines are then provided with comparators 16 and 18, each of which yields a low output until it receives a heart beat pulse, at which time its output switches to a high for the duration of the heart beat pulse. The outputs of the comparators are applied respectively to one-shot circuits 20 and 22 which are triggered when the comparator outputs go high. The one-shot circuits are identical and provide 250 millisecond outputs, wherein the output signals of the respective one-shot circuits are designated as ECG-REF and P/P REF. The 250 millisecond period of each of the one-shots 20 and 22 provides a substantial output pulse for use by the succeeding circuitry, and such period also precludes double or false triggering for a substantial length of time following the reception of a heart beat signal.

The one shot-outputs are applied to a multiplex circuit 24 which is controlled by the selection circuitry to provide the selected output to the rate monitoring circuit in response to an output from a microprocessor 26. The microprocessor may take the form, for example, of a Type 3870 device.

The two reference signals from the respective one-shot circuits, namely the ECG-REF and the P/P REF signals, are also applied respectively to a pair of flip-flop circuits 28 and 39 having their outputs connected through a buss transceiver 32 to the microprocessor 26, and to a pair of 3 count counters 34 and 36. The reset inputs for the flip-flops are connected through a decoder 38 from the microprocessor 26, also by means of the buss transceiver 32.

The outputs of the two 3-count counters 34 and 36 are read by the microprocessor 26 to determine whether the counters have counted three requests or no requests during a selected period. In this regard, the microprocessor is capable of asynchronously reading the various signals generated by the automatic trigger circuitry, and is capable of making determinations of request signals, three consecutive requests, and no requests.

In accordance with the operation of the logic circuitry illustrated in FIG. 1 of the drawings, an ECG-REF or P/P-REF signal will cause its respective flip-flop to be set and to generate an ECG-REQ signal or a P/P-REQ signal, which signals are referred to as "request" signals. Such request signals are applied to the microprocessor 26 through the buss 32, and are also applied to the 3-count counters for causing the latter of increment. Furthermore, the generation of a request signal causes the decoder circuit 38 to reset the related flip-flop 28 or 30 in preparation for receipt of the next heart beat signal from one of the one-shot circuits.

In the microprocessor the successive request signals cause respective interval timers first to start a count up period, then to decrement, and then to stop. Accordingly, if at the time of receipt of the request signal, the corresponding interval timer in the microprocessor is in its stop mode, such timer will be initialized at zero and will begin counting at a rate of 60 counts per second. On the other hand, in the event the timer is already running, as will be the case if the request signal is the second in a series of three request signals, then the microprocessor will cause the timer to begin decrementing. Upon receipt of the third request signal in a series of three, the internal timer is switched to its stop mode, and the microprocessor functions to determine if the outer source is active or inactive. If inactive, then the microprocessor 26 will select the active channel as the output to be provided by the multiplex circuit 24 to the rate meter circuit. If the other channel is active, then the microprocessor will select the output from the ECG channel if the deviation between the count-up and count down of the channel is less than 16 counts. However, if the deviation is greater than 16 counts, then a comparison is made with the deviation of the P/P source channel whereupon the channel having the lower deviation is selected by the multiplex circuit 24.

Figure 2:
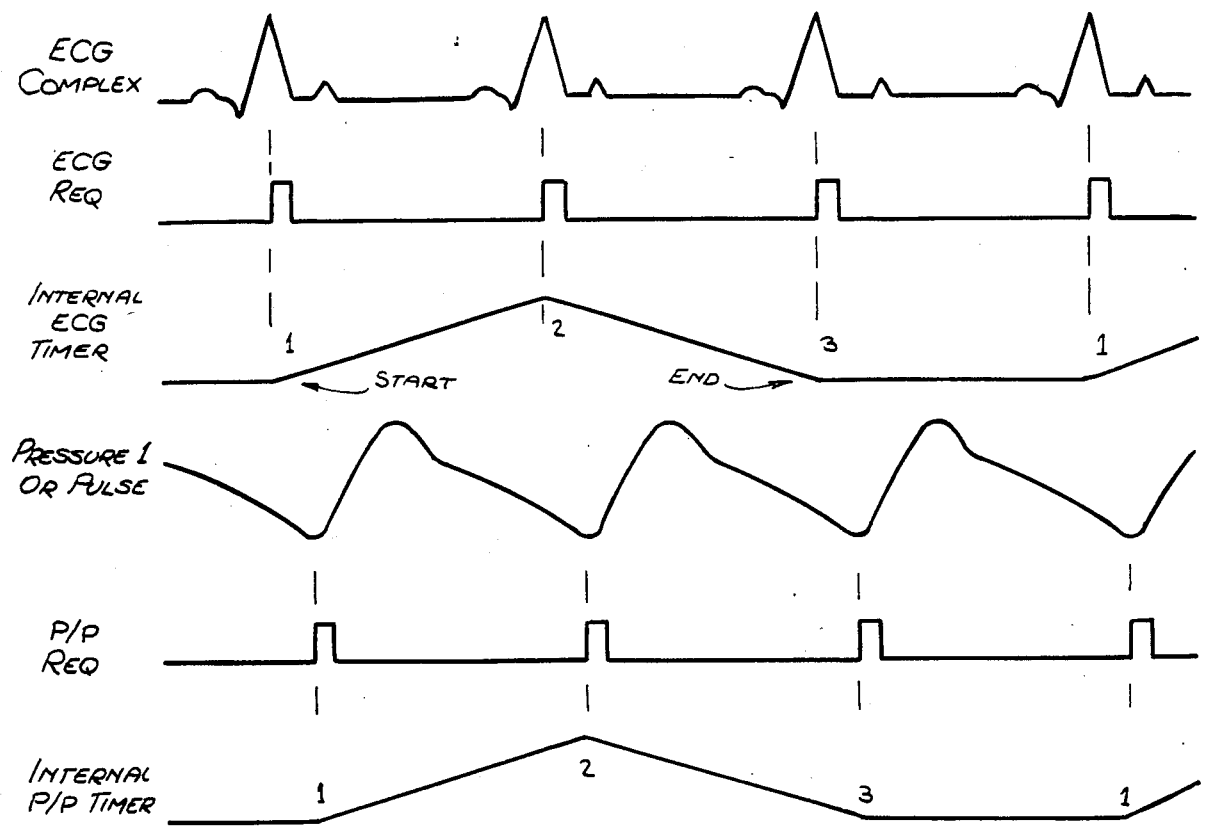
FIG. 2 is a timing diagram showing various waveforms of the circuitry described with respect to FIG. 1.

In this regard, FIG. 2 illustrates the various waveforms referred to above, wherein the ECG and P/P waveforms are shown in conjunction with their associated flip-flop request signals, and the count-up and count-down periods of the microprocessor. In accordance with the various waveforms shown in that drawing, it will be appreciated that the peak or r-portion of the ECG complex corresponds to the initiation of the ECG-REQ pulse, and that the timing of the internal counter of the microprocessor 26 commences at the same time. Similarly, the beginning of decrement counting occurs at the r-portion of the next successive heart beat detected on the ECG line, and the counting is stopped at the r-portion of the third ECG complex heart beat signal. The counter then remains dormant until the next r-portion of a heart beat at which time the counter again commences its upward count. These same relationships exist with respect to the pressure pulse source, but in that case the trigger point for the one-shot and the flip-flop occurs at the beginning of systole, at which time the pressure/pulse signal begins its positive ascent.

Figure 6:
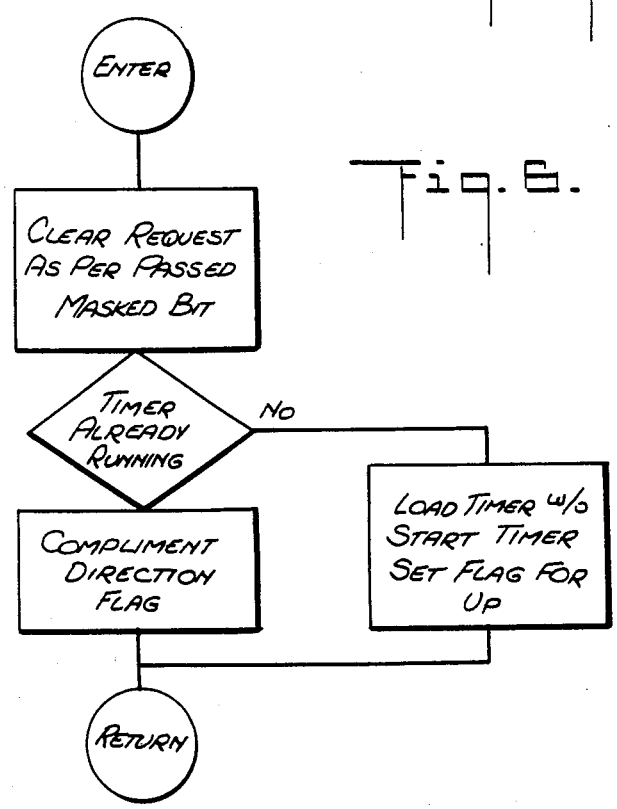
Figure 4:
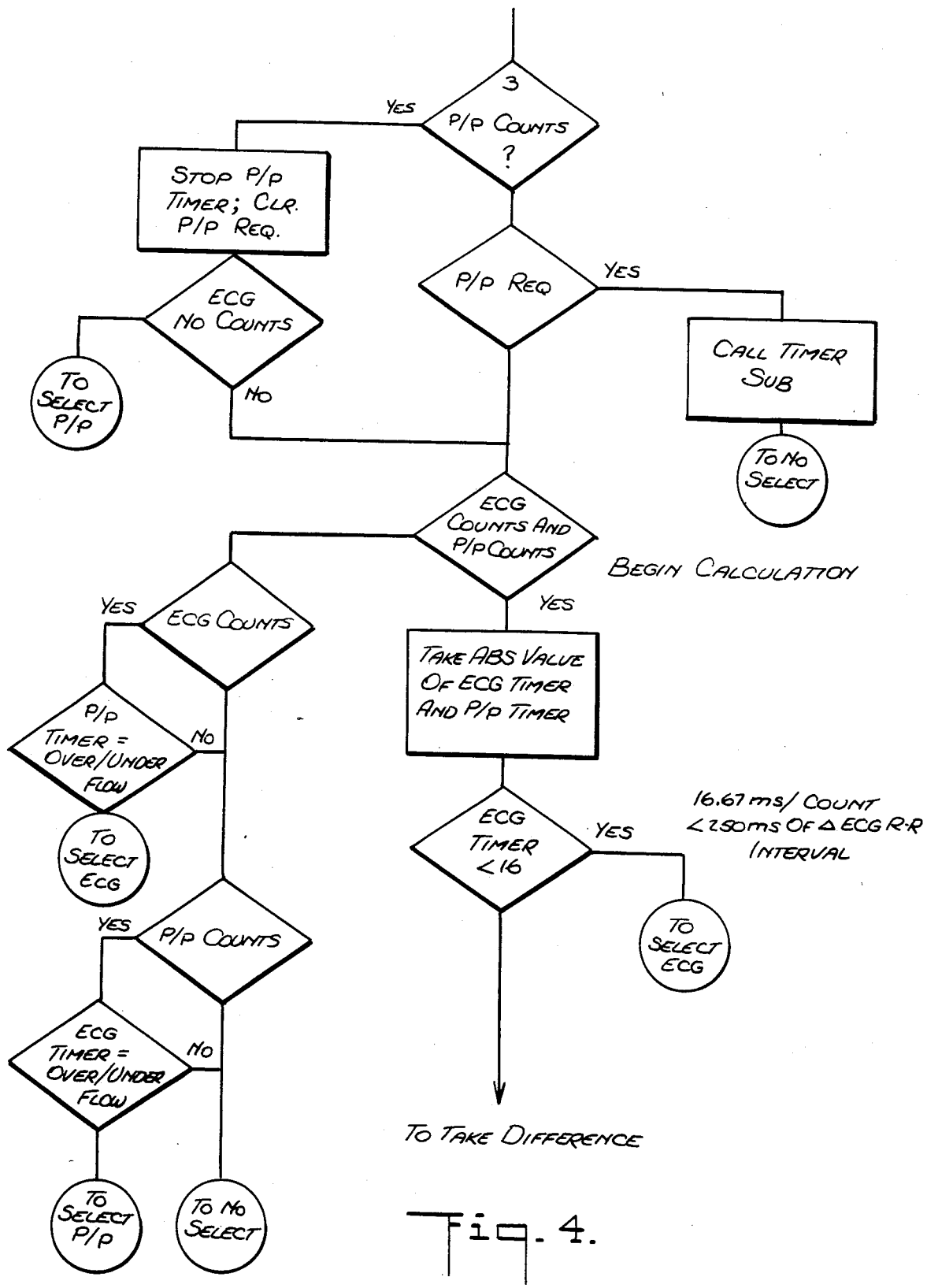

In accordance with the preferred embodiment of the invention, FIGS. 3, 4 and 5 disclose flow charts of the operation of the microprocessor, wherein FIG. 3 illustrates an initialization procedure in which the microprocessor 26 enables the buss transceiver, and reads and temporarily stores data from the logic circuitry. An initial determination is made as to whether or not one of the pressure/pulse sources is plugged into the system, and if faults exist in ECG source lines, so that an adequate selection can be made. In the next step, the counters are read, and if a 3-count output is detected then a stop signal is generated for the ECG internal timer of the microprocessor, and a clear ECG request signal is generated, whereas if any REQ signals are produced without a reading from either of the two 3-count counters, then the timer sub program is called as illustrated in FIG. 6. If no counts are read by the pressure/pulse source then the ECG source line is selected. As shown in FIG. 4, this same process is performed with respect to the P/P line wherein if three counts are detected from the pressure/pulse 3-count counter, then a stop signal is applied to the pressure/pulse timer of the microprocessor, and a clear signal is generated for application to the flip-flop of the P/P line.

If only one or the other of a 3-count signals is produced by the 3-count counters, then the source corresponding to the detected 3-count is selected. However, if both of the 3-count counters provide outputs, then the count-up and count-down of both of the ECG and pressure/pulse timers are determined. Under these conditions, if the difference between ECG count-up and count-down pulses is less than 16, the ECG source is selected by the multiplex. In this regard, the count of 16 was chosen due to the fact that 16 counts of a 60 cycle counting timer equals approximately 250 milliseconds, which has been determined to be a permissible variation in time between adjacent heart beat signals.

As illustrated by the flow chart of FIG. 4, at the lower-center portion thereof, if the difference between count-up and count-down of the ECG circuit exceeds a count of 16, then a difference calculation is made to determine which of the deviations of the two timers in he microprocessor is smaller, and the procedure for such a determination is set forth in FIG. 5.

It will be appreciated by those skilled in the art that modifications of the preferred embodiment of the invention may be made, but that such modifications will fall within the scope of the present invention as defined in the following claims.

We claim:

1. An automatic pulse rate trigger-source select circuit, for selecting between trigger pulses corresponding to an ECG heart rate signal source and trigger pulses corresponding to a pressure/pulse heart rate signal source, and for providing the selected trigger pulses as an output signal, comprising:

input means having inputs for being coupled to said original sources for generating said respective trigger pulses;

comparison circuit means, coupled to receive said trigger pulses from said input means, for comparing successive periods between trigger pulses for both of said sources to determine which of said sources is most accurately periodic, wherein said comparison circuit means provides an output instruction signal in correspondence with the said most periodic source, and wherein said comparison circuit means comprises a microprocessor programmed to provide a pair of timer functions for respectively counting up during a first of two successive heart beat periods for each of said sources, and for counting down during the second of said successive periods, and programmed to compare the final counts of said timer functions at the completion of said respective second periods; and selecting circuit means, coupled to receive said trigger pulses from said input means, and coupled to receive said instruction signal from said comparison circuit means for selecting the trigger pulse corresponding to one of said sources of heart beat signals in response to said output instruction signal, and for providing the selected trigger pulses as an output signal corresponding to the selected source; wherein said trigger pulses provided as an output signal are selected automatically in correspondence with the most periodic of said sources.

2. An automatic pulse rate trigger-source select circuit, as set forth in claim 1, wherein said input means comprises first and second one-shot circuits, for being respectively coupled to said ECG and said pressure/pulse sources of heart beat signals, said one-shot circuits having set periods of the order of 250 milliseconds, and being set respectively at the r-portion of the ECG wave and at the beginning of systole of said pressure/pulse source to protect against false triggering, and wherein the outputs of said first and second one-shot circuits comprise said trigger pulses corresponding to said ECG heart rate signal source and said pressure/pulse heart rate signal source.

3. An automatic pulse rate trigger-source select circuit as set forth in claim 1, wherein said selecting circuit comprises a multiplex circuit for providing said trigger pulses as an output signal, corresponding to one of said sources, in response to said output instruction signal from said comparison circuit means.

4. An automatic pulse rate trigger-source select circuit as set forth in claim 1, wherein said comparison circuit means further comprises means for generating said output instruction signal to select said trigger pulses provided as an output signal to correspond to said ECG source if said final count of the ECG timer is below a predetermined count.

* * * * *

UNITED STATES PATENT AND TRADEMARK OFFICE
CERTIFICATE OF CORRECTION

PATENT NO. : 4,573,478

DATED : March 4, 1986

INVENTOR(S) : JEFFREY M. ARNOLD, ET AL.

It is certified that error appears in the above-identified patent and that said Letters Patent is hereby corrected as shown below:

COVER PAGE DRAWING

"BUS TRANCEIVER" should read --BUS TRANSCEIVER--.

IN THE DRAWINGS

FIG.1, "BUS TRANCEIVER" should read --BUS TRANSCEIVER--.

COLUMN 1

Line 60, "peridicity" should read --periodicity--.
Line 63, "changes" should read --chances--.

COLUMN 2

Line 1, "DRAWING" should read --DRAWINGS--.
Line 47, "one shot-outputs" should read --one-shot outputs--.
Line 56, "28 and 39" should read --28 and 30--.

UNITED STATES PATENT AND TRADEMARK OFFICE
CERTIFICATE OF CORRECTION

PATENT NO. : 4,573,478

DATED : March 4, 1986

INVENTOR(S) : JEFFREY M. ARNOLD, ET AL.

It is certified that error appears in the above-identified patent and that said Letters Patent is hereby corrected as shown below:

COLUMN 3

Line 10-11, "latter of increment" should read --latter to increment--.

Line 28, "outer" should read --other--.

COLUMN 4

Line 36, "he microprocessor" should read --the microprocessor--.

Signed and Sealed this

Seventeenth Day of February, 1987

Attest:

DONALD J. QUIGG

Attesting Officer     Commissioner of Patents and Trademarks